(12) United States Patent
Kitamura et al.

(10) Patent No.: US 11,096,751 B2
(45) Date of Patent: Aug. 24, 2021

(54) PUNCTURE ROBOT

(71) Applicant: NATIONAL UNIVERSITY CORPORATION OKAYAMA UNIVERSITY, Okayama (JP)

(72) Inventors: Hiroki Kitamura, Okayama (JP); Akira Heya, Okayama (JP); Takafumi Namba, Okayama (JP); Tetsushi Kamegawa, Okayama (JP); Takayuki Matsuno, Okayama (JP); Takao Hiraki, Okayama (JP)

(73) Assignee: NATIONAL UNIVERSITY CORPORATION, OKAYAMA UNIVERSITY, Okayama (JP)

( * ) Notice: Subject to any disclaimer, the term of this patent is extended or adjusted under 35 U.S.C. 154(b) by 320 days.

(21) Appl. No.: 15/767,855

(22) PCT Filed: Sep. 29, 2016

(86) PCT No.: PCT/JP2016/078920
§ 371 (c)(1),
(2) Date: Apr. 12, 2018

(87) PCT Pub. No.: WO2017/065016
PCT Pub. Date: Apr. 20, 2017

(65) Prior Publication Data
US 2018/0206926 A1 Jul. 26, 2018

(30) Foreign Application Priority Data
Oct. 13, 2015 (JP) .............................. JP2015-202482

(51) Int. Cl.
*A61B 34/35* (2016.01)
*A61B 90/11* (2016.01)
(Continued)

(52) U.S. Cl.
CPC .............. *A61B 34/35* (2016.02); *A61B 17/34* (2013.01); *A61B 18/1477* (2013.01);
(Continued)

(58) Field of Classification Search
CPC ................ A61B 17/34; A61B 18/1477; A61B 2017/3409; A61B 2018/0293;
(Continued)

(56) References Cited

U.S. PATENT DOCUMENTS 5,397,323 A * 3/1995 Taylor .................. B25J 19/0008
606/130
5,836,869 A 11/1998 Kudo et al.
(Continued)

FOREIGN PATENT DOCUMENTS

| JP | H08164148 A | 6/1996 |
|----|-------------|--------|
| JP | 2002530209 A | 9/2002 |

(Continued)

OTHER PUBLICATIONS

International Search Report corresponding to Application No. PCT/JP2016/078920; dated Dec. 27, 2016.

*Primary Examiner* — Kathleen S Holwerda
*Assistant Examiner* — Brooke Labranche
(74) *Attorney, Agent, or Firm* — Cantor Colburn LLP

(57) ABSTRACT

The invention may provide a puncture robot that can precisely move a needle in the puncture direction by setting needle position in a CT gantry. Provided is a puncture robot comprising a puncture unit, puncture robot being configured such that: the puncture unit comprises a puncture needle, an arm unit, a frame unit, and a base unit; the frame unit comprises a first frame and a second frame that are each provided with an advancing and retracting shaft, and a connecting rod; the arm unit comprises an upper arm and a lower arm, with the puncture needle being mounted to be (Continued)

parallel to the advancing and retracting shaft and the upper arm and the lower arm are advanced and retracted along the advancing and retracting shaft.

5 Claims, 11 Drawing Sheets

(51) Int. Cl.
  *A61B 18/14* (2006.01)
  *A61B 34/30* (2016.01)
  *A61B 17/34* (2006.01)
  *A61B 90/00* (2016.01)
  *A61B 18/02* (2006.01)

(52) U.S. Cl.
  CPC .............. *A61B 34/30* (2016.02); *A61B 90/11* (2016.02); *A61B 2017/3409* (2013.01); *A61B 2018/0293* (2013.01); *A61B 2090/065* (2016.02); *A61B 2090/3762* (2016.02)

(58) Field of Classification Search
  CPC ...... A61B 2090/065; A61B 2090/3762; A61B 34/30; A61B 34/35; A61B 90/11
  See application file for complete search history.

(56) References Cited

U.S. PATENT DOCUMENTS

| | | |
|---|---|---|
| 6,036,637 A | 3/2000 | Kudo |
| 6,723,106 B1 | 4/2004 | Charles et al. |
| 7,922,688 B2 | 4/2011 | Bodduluri et al. |
| 9,326,822 B2 | 5/2016 | Lewis et al. |
| 2004/0024385 A1* | 2/2004 | Stuart .................. B25J 17/0266 606/1 |
| 2008/0167674 A1 | 7/2008 | Bodduluri et al. |
| 2011/0160745 A1* | 6/2011 | Fielding ................. A61B 34/37 606/130 |
| 2014/0277333 A1 | 9/2014 | Lewis et al. |
| 2016/0228189 A1* | 8/2016 | Goldenberg ........... A61B 34/30 |
| 2016/0235946 A1 | 8/2016 | Lewis et al. |
| 2016/0249991 A1 | 9/2016 | Glozman et al. |

FOREIGN PATENT DOCUMENTS

| | | |
|---|---|---|
| JP | 2013009919 A | 1/2013 |
| WO | 2015052718 A1 | 4/2015 |

* cited by examiner

PUNCTURE ROBOT

CROSS REFERENCE TO RELATED APPLICATIONS

This is the U.S. national stage of application No. PCT/JP2016/078920, filed on Sep. 29, 2016. Priority under 35 U.S.C. § 119(a) and 35 U.S.C. § 365(b) is claimed from Japanese Application No. 2015-202482, filed on Oct. 13, 2015, the disclosure of which is also incorporated herein by reference.

TECHNICAL FIELD

The present invention relates to a puncture robot, particularly to a puncture robot used to puncture a lesioned portion such as a tumor using a puncture needle under X-ray fluoroscopy by CT (Computed Tomography).

BACKGROUND ART

Radiofrequency therapy, cryotherapy, biopsy, drainage, and the like are performed in a wide range of interventions performed by puncturing the lesioned portion using the puncture needle under CT fluoroscopic guidance, and recently this technique is widely practiced. For example, in the radiofrequency therapy, a radiofrequency current is passed through the tumor while the tumor is punched using the puncture needle for radiofrequency therapy, and it is necessary to accurately puncture the tumor using a puncture needle. For this reason, the puncture is performed while a position of the tumor and a position of the puncture needle are checked under the X-ray fluoroscopy by CT.

What is called CT guided biopsy, in which a tissue is sampled and examined by puncturing the tumor or the like in a body using the puncture needle under the X-ray fluoroscopy by CT, is performed. In the CT guided biopsy, it is also necessary to accurately puncture the tumor using the puncture needle. For this reason, the puncture is performed while a position of the tumor and a position of the puncture needle are checked under the X-ray fluoroscopy by CT.

The puncture work is manually performed by a practitioner in a vicinity of a CT gantry irradiating the tumor with an X-ray, and the body of the practitioner, such as the hand supporting the puncture needle, may be exposed to the X-ray. For this reason, the practitioner works while wearing an apron containing lead to avoid X-ray exposure of the practitioner as much as possible, but it is difficult to completely eliminate the X-ray exposure.

Thus, there is a demand for developing a robot that performs the puncture work instead of the practitioner.

There has been proposed a puncture system, in which a pressure sensor that detects a puncture pressure is provided in an epidural needle which punctures an epidural space rather than the puncture needle used in the radiofrequency therapy or the CT guided biopsy and the pressure sensor detects the moment when a needle point of the epidural needle reaches the epidural space (for example, see Patent Document 1). However, the puncture work is performed by the practitioner.

In view of such present situations, the present inventors have started to develop a robot that performs the puncture work by remote operation by the practitioner.

PRIOR ART DOCUMENT

Patent Document

Patent Document 1: JP-A 2013-009919 Gazette

SUMMARY OF THE INVENTION

Problems to be Solved by the Invention

When the puncture work is performed under the X-ray fluoroscopy by CT, it is necessary to set a position and a posture of the needle in a small space of the CT gantry. Consequently, in order to decide the posture of the needle, it is necessary to set a rotation center to the vicinity of the needle.

On the other hand, because the existence of a metal material in the CT gantry causes an artifact to adversely affect a CT image, a drive motor that rotates the needle or a sensor cannot be disposed near the needle.

A certain degree of a puncturing speed and linear motion accuracy of the puncture are required in order that the needle easily penetrates regions that frequently move such as a skin and a tumor. Because there is a possibility that the puncture needle may be deflected when the puncture needle comes into contact with a bone or the like by mistake, it is necessary to attach a sensor that detects the deflection of the puncture needle.

When the puncture needle is moved in a puncture direction as soon as possible, a vibration is easily generated in the puncture needle, the vibration may cause the needle tip to escape from the tumor, and it is necessary to move the puncture needle in the puncture direction as soon as possible while the vibration is prevented.

Solutions to the Problems

The puncture robot according to one aspect of the present invention includes: a robot body; and a puncture unit attached to a moving end, the moving end being included in the robot body and movable in any direction. The puncture unit includes: an arm in which a puncture needle is attached to a leading end of the arm; a frame to which a base end of the arm is attached; and a base that supports the frame.

In particular, the frame of the puncture robot includes a first frame, a second frame, and a connecting rod, each of the first frame and the second frame having a rectangular frame shape and having an advancing and retracting shaft extending in a vertical direction being provided inside of the frame, the connecting rod connecting the first frame and the second frame while the first frame and the second frame are opposite each other, the arm includes an upper arm for supporting a base end side of the puncture needle and a lower arm for supporting a leading end side of the puncture needle with respect to a portion supported by the upper arm, and holds the puncture needle attached in parallel to the advancing and retracting shafts, and the puncture needle is advanced and retracted in a puncture direction by advancing and retracting the upper arm and the lower arm along the advancing and retracting shafts.

In the puncture robot, a first sensor constructed with a six-axis force sensor is provided in a middle portion of the upper arm, and a second sensor constructed with a six-axis force sensor is provided in a middle portion of the lower arm, and the upper arm and the lower arm are bent in a crank shape to offset the puncture needle in the puncture direction.

In the puncture robot, in the upper arm and the lower arm, a portion that is closer to the puncture needle than the first sensor and the second sensor is made of a resin material.

According to another aspect of the present invention, the frame of the puncture robot includes a first frame, a second frame, and a connecting rod, each of the first frame and the second frame having a rectangular frame shape and having an advancing and retracting shaft extending in a vertical direction being provided inside of the frame, the connecting rod connecting the first frame and the second frame while the first frame and the second frame are opposite each other, the arm holds the puncture needle attached in parallel to the advancing and retracting shafts, and includes an actuator in a middle portion of the arm for advancing and retracting the puncture needle in a puncture direction, the puncture needle is advanced and retracted in a vicinity of a puncture region by advancing and retracting the upper arm and the lower arm along the advancing and retracting shafts, and the puncture region is instantaneously punctured by instantaneously driving the actuator during a puncture operation of the puncture needle in the vicinity of the puncture region.

In the puncture robot, in the arm, two sensors each constructed with a six-axis force sensor are provided in a middle portion of the arm while stacked.

In the puncture robot, the arm includes a needle grip that grips the puncture needle at the leading end of the arm, and the needle grip is detachable with respect to the arm.

In the puncture robot, the needle grip is made of a resin material.

Effects of the Invention

According to the present invention, the frame is constructed with the first frame, the second frame, and the connecting rod, each of the first frame and the second frame having the rectangular frame shape and having the advancing and retracting shaft extending in a vertical direction being provided inside of the frame, the connecting rod connecting the first frame and the second frame while the first frame and the second frame are opposite each other, and the frame holds the puncture needle attached in parallel to the advancing and retracting shafts, and the upper arm and the lower arm are advanced and retracted along the advancing and retracting shaft. Consequently, the advancing and retracting movement and the posture change of the puncture needle can be performed from a position separated from the puncture needle even if the puncture work is performed in the small space.

EMBODIMENTS OF THE INVENTION

Hereinafter, embodiments of the present invention will be described with reference to the drawings.

Embodiment 1

Figure 1:
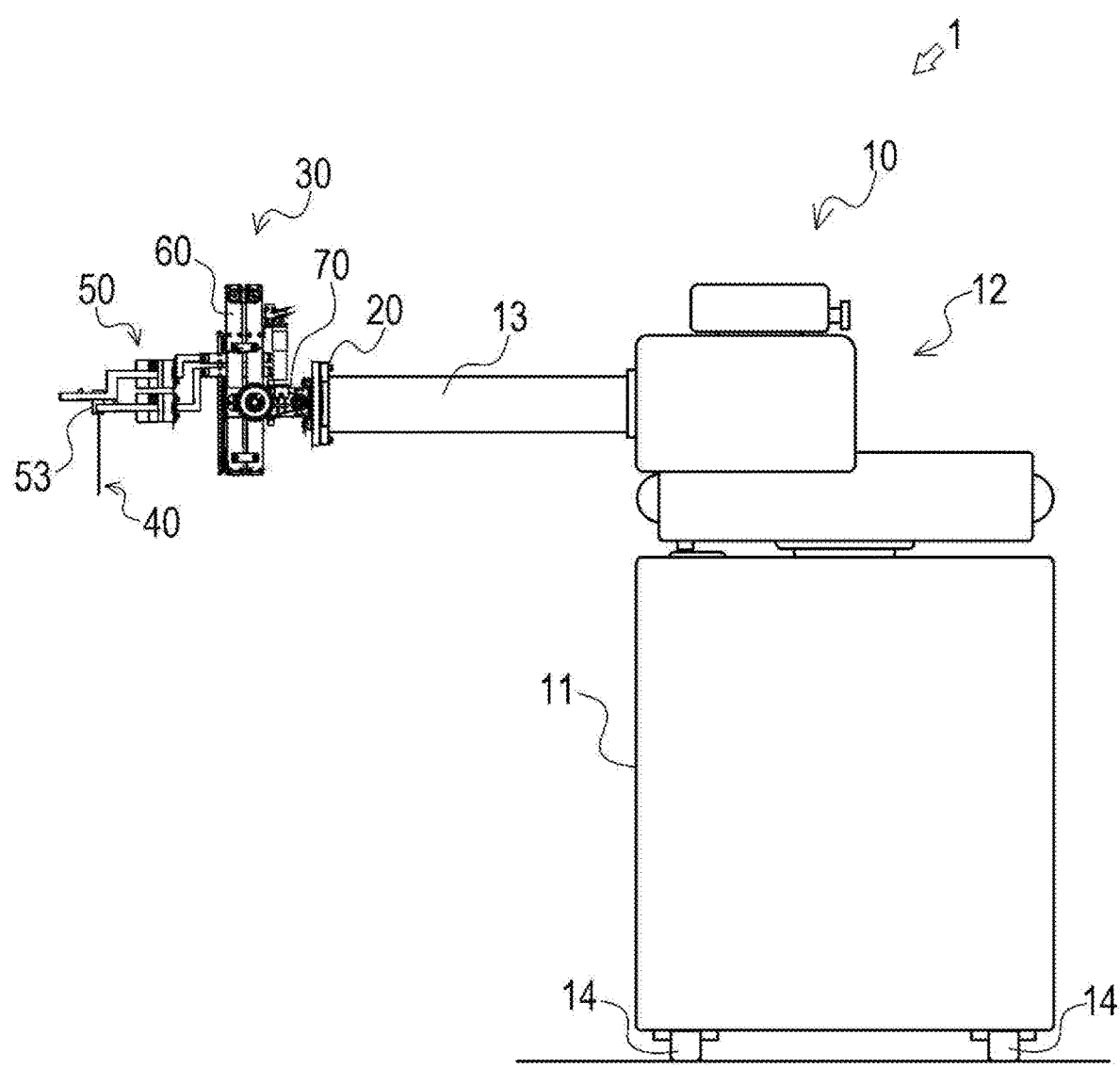
FIG. 1 is a side view illustrating a puncture robot according to Embodiment 1 of the present invention.

As illustrated in FIG. 1, a puncture robot 1 according to Embodiment 1 has a robot body 10 and a puncture unit 30 attached to a moving end 20 that is provided to the robot body 10 and is movable in any direction. The puncture unit 30 is a portion constituting an instrument of the robot body 10.

The robot body 10 includes a casing 11 having a rectangular parallelepiped shape, a driver 12 disposed above the casing 11, and a connecting rod 13 horizontally attached to one end of the driver 12, a leading end side of the connecting rod 13 extending to an outside of the casing 11. The robot body 10 includes a handle (not illustrated) provided at an upper end of a side surface of the casing 11 and a plurality of casters 14 provided in a bottom portion of the casing 11, and a user grips the handle to freely move the robot body 10. The driver 12 moves a flange-shaped moving end 20 provided at the leading end of the connecting rod 13 using a plurality of actuators (not illustrated) in three dimensions of an advancing and retracting direction, a vertical direction (elevation direction), and a crosswise direction. In the robot body 10, the moving end 20 is moved in the advancing and retracting direction, the vertical direction, and the crosswise direction by a linear motion joint. The driver 12 can rotate the connecting rod 13 about an axis of the connecting rod 13A by an actuator (not illustrated). The robot body 10 drives the driver 12 to move the puncture unit 30 attached to the moving end 20 provided at the leading end of the connecting rod 13 to a desired position. The robot body 10 moves the puncture unit 30 in the advancing and retracting direction, the vertical direction, and the crosswise direction by operating the linear motion joint, whereby the puncture unit 30 can be moved in a stable orbit even in a small space such as a vicinity of a CT gantry.

The puncture unit 30 is attached to the moving end 20 disposed at the leading end of the connecting rod 13.

Figure 2:
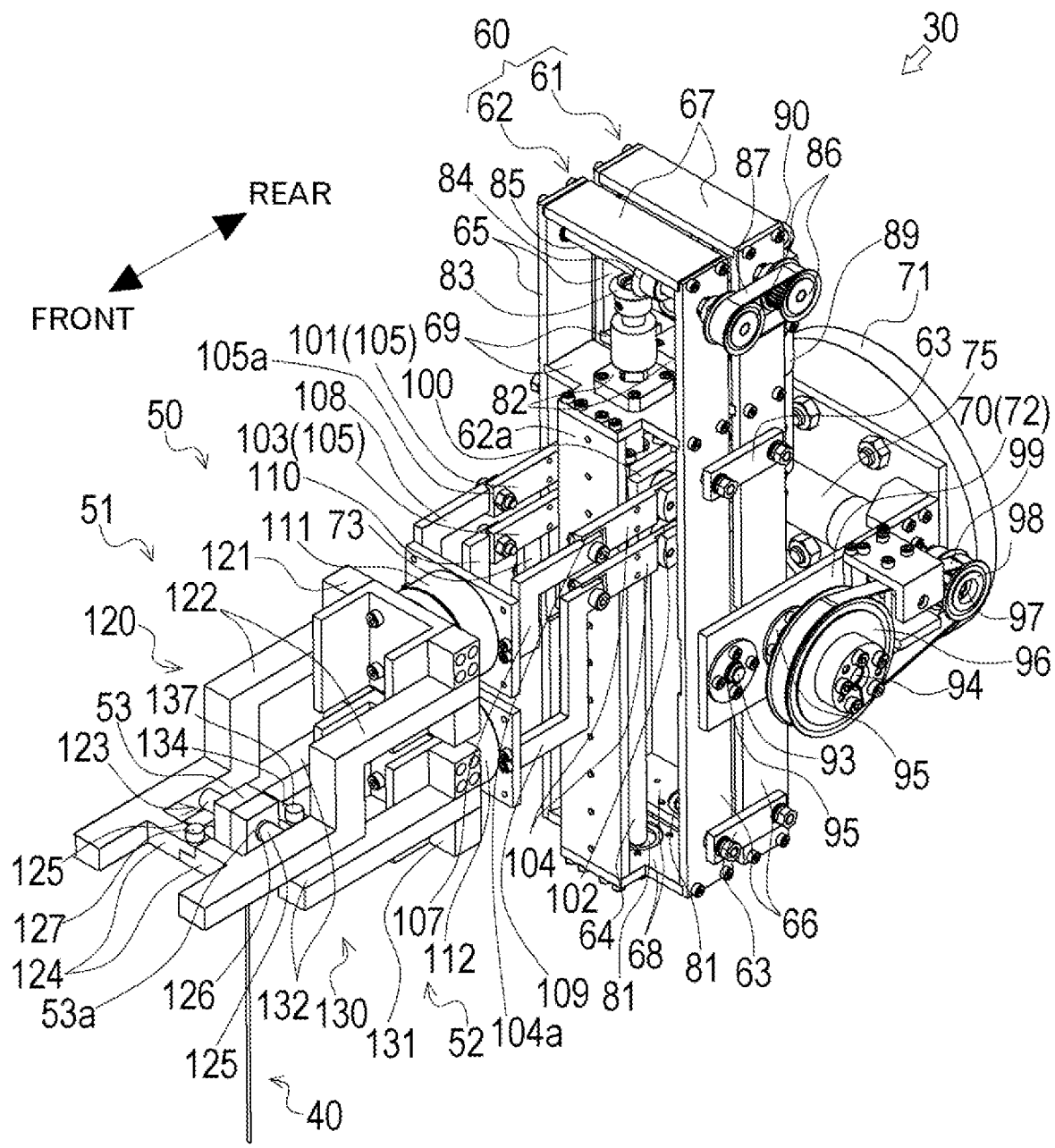
FIG. 2 is a perspective view illustrating a puncture unit of Example 1.
Figure 3:
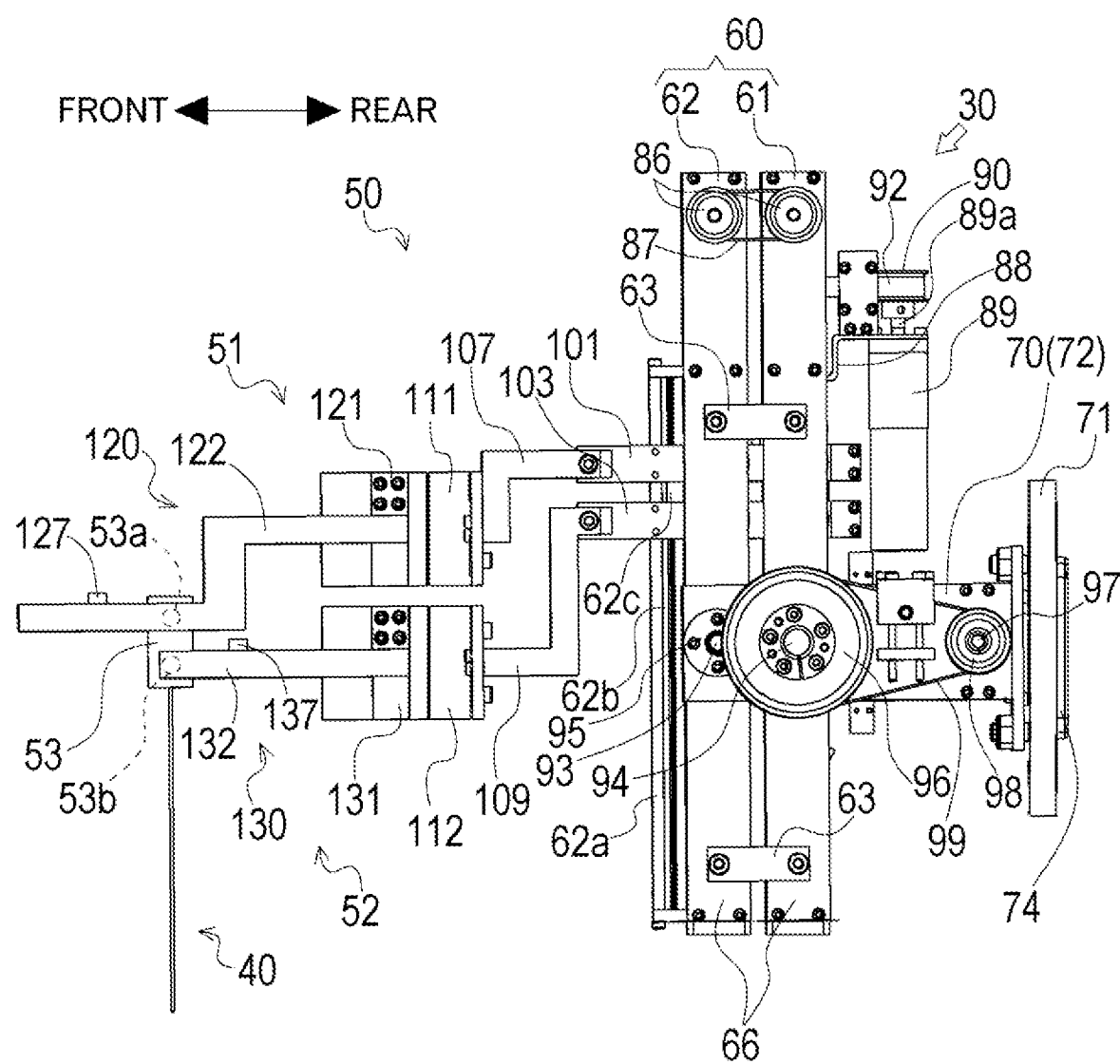
FIG. 3 is a side view illustrating the puncture unit of Example 1.
Figure 4:
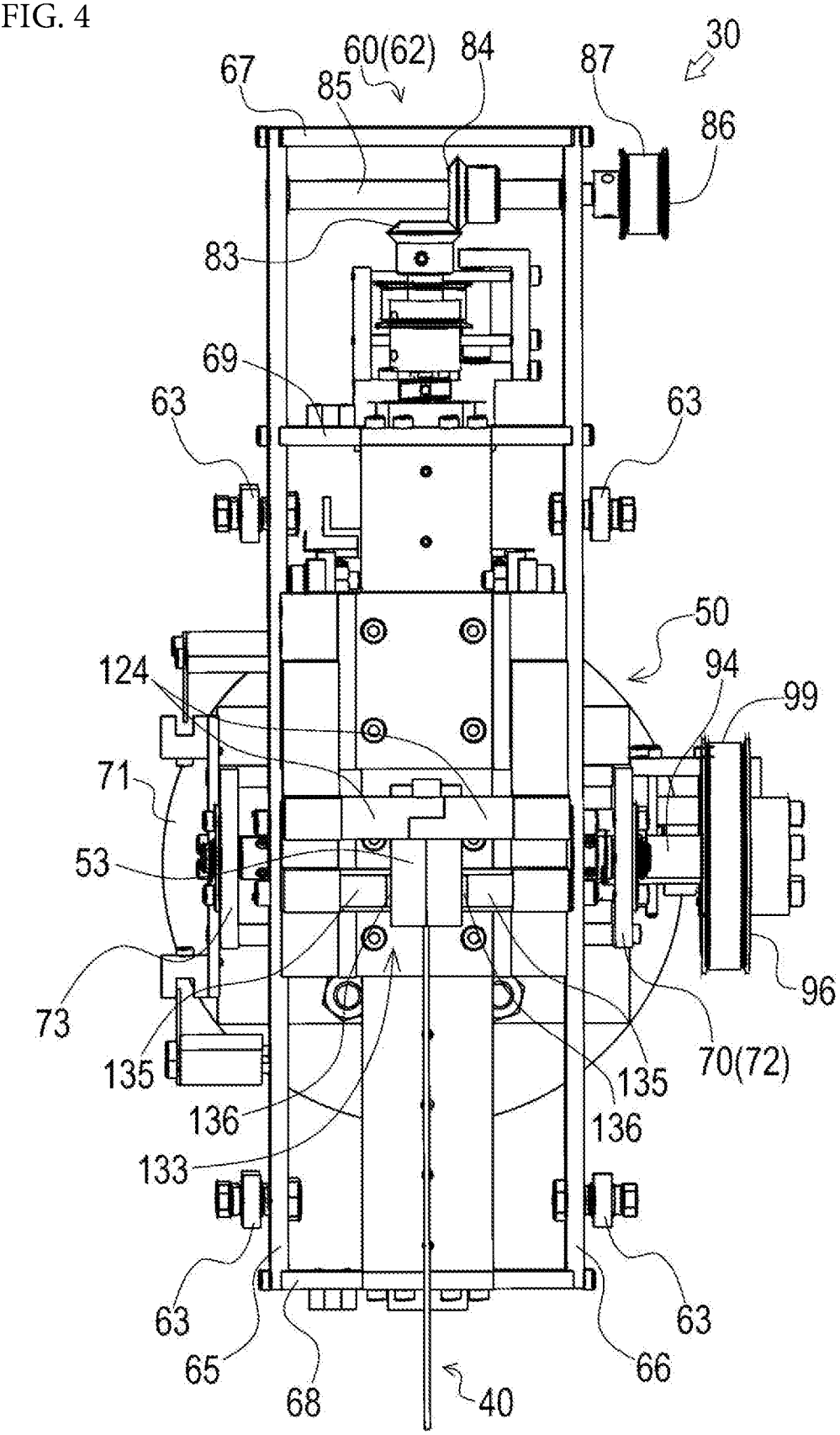
FIG. 4 is a front view illustrating the puncture unit of Example 1.
Figure 5:
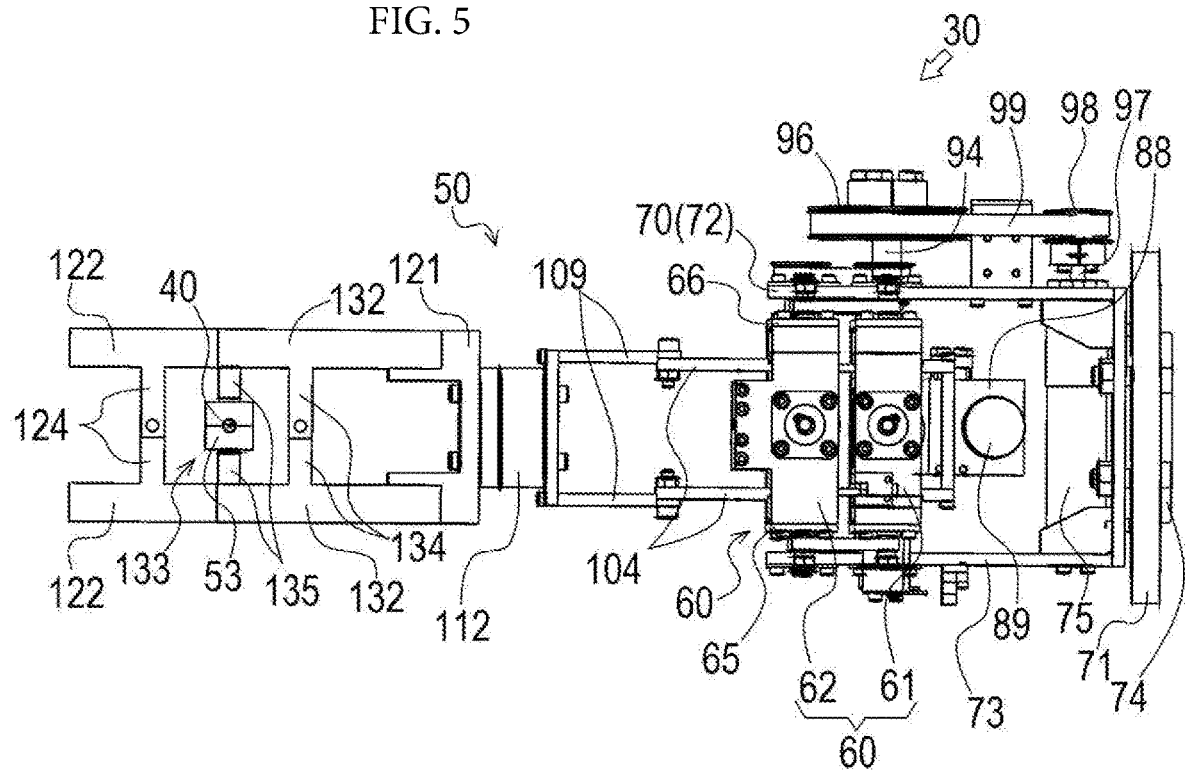
FIG. 5 is a bottom view illustrating the puncture unit of Example 1.
Figure 6:
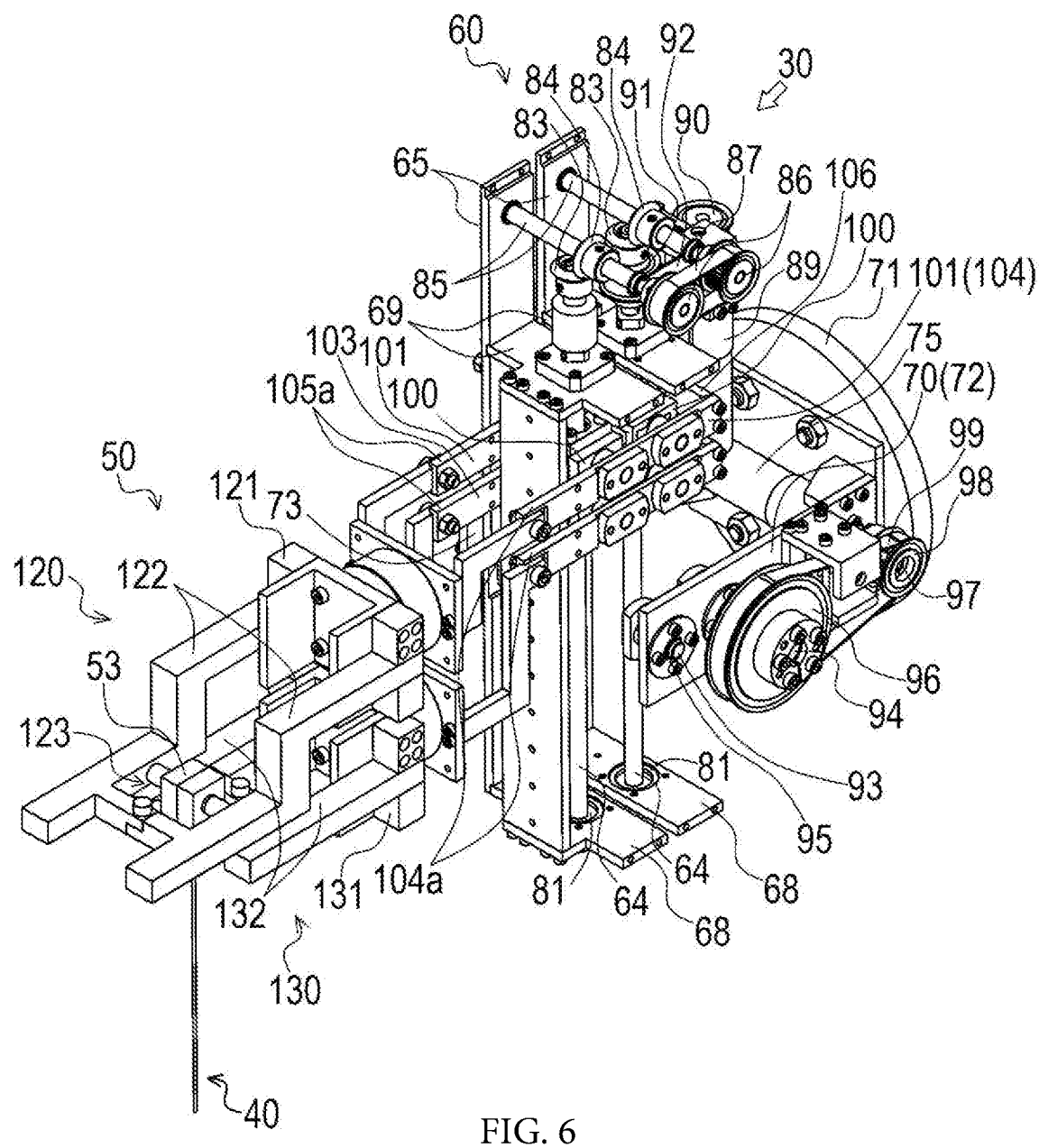
FIG. 6 is a perspective view illustrating the puncture unit of Example 1 while a part of a frame is removed in FIG. 2.

In the puncture unit 30, it is assumed that a direction of a double-headed arrow in FIG. 2 and FIG. 3 is a front-back direction.

As illustrated in FIG. 2 to FIG. 6, the puncture unit 30 includes an arm 50 the leading end of which has a puncture needle 40 is attached thereto, a frame 60 to which a base end of the arm 50 is attached, and a base 70 supporting the frame 60. The puncture unit 30 is fixedly attached to the moving end 20 of the connecting rod 13 via the base 70. Thus, when the connecting rod 13 is rotated about the axis by a connecting rod rotating actuator (not illustrated) included in the robot body 10, the puncture unit 30 rotates with the connecting rod 13 as a rotation shaft.

The base 70 includes a disk-shaped base end plate 71 to which the moving end 20 at the leading end of the connecting rod 13 is attached and a flat first support piece 72 and a flat second support piece 73, which extend forward from both left and right ends of the base end plate 71 to movably support the frame 60. The base 70 has a substantially U-shape in plan view.

A guide 74 to which the leading end of the connecting rod 13 is attached is provided on a rear side of the base end plate 71. Positioning is performed by attaching the leading end of the connecting rod 13 to the guide 74, and a clamp screw is screwed from a rear end face of the flange-shaped moving end 20 to fix the puncture unit 30 to the leading end of the moving end 20.

A frame rotating motor 75 that rotates the frame 60 is attached to a front side of the base end plate 71 as described later.

The frame 60 includes a first frame 61, a second frame 62, and a plurality of connecting rods 63. Each of the first frame 61 and the second frame 62 has a rectangular frame shape, and an advancing and retracting shaft 64 (for example, a threaded shaft of a ball screw) extending in a vertical direction is provided inside each of the first frame 61 and the second frame 62. The plurality of connecting rods 63 connect the first frame 61 and the second frame 62 while the first frame 61 and the second frame 62 face each other. In particular, a parallel link is formed by connecting the first frame 61 and the second frame 62 using the connecting rods 63.

The first frame 61 and the second frame 62 have the same structure, and the first frame 61 will be described below as a representative.

The first frame 61 includes a first side wall 65, a second side wall 66, a third side wall 67, and a fourth side wall 68. The first side wall 65 and the second side wall 66 have a flat plate shape, and extend in the vertical direction while facing each other. The third side wall 67 has a flat plate shape, and connects upper end edges of the first side wall 65 and the second side wall 66. The fourth side wall 68 has a flat plate shape, and connects lower end edges of the first side wall 65 and the second side wall 66. The first frame 61 is formed into a vertically elongated rectangular frame shape.

In the first frame 61, an intermediate wall 69 is provided between the first side wall 65 and the second side wall 66, which are close to the third side wall 67.

A lower bearing 81 and an upper bearing 82, which support the advancing and retracting shaft 64 extending in the vertical direction in parallel with the first side wall 65 and the second side wall 66, are provided in the fourth side wall 68 and the intermediate wall 69, respectively, and the advancing and retracting shaft 64 is pivotally supported by the lower bearing 81 and the upper bearing 82.

The advancing and retracting shaft 64 extends so as to protrude upward from the upper bearing 82, and a first bevel gear 83 is attached to the upper end of the upwardly protruding advancing and retracting shaft 64.

A second bevel gear 84 engaging with the first bevel gear 83 is attached to a rotation shaft 85 rotatably mounted on the first side wall 65 and the second side wall 66 above the first bevel gear 83.

An end of the rotation shaft 85 on the side of the second side wall 66 extends so as to protrude outward, and an interlocking pulley 86 is attached to the protruding rotation shaft 85. The interlocking pulley 86 of the first frame 61 and the interlocking pulley 86 of the second frame 62 have the same shape, and are interlocked with each other via an interlocking timing belt 87.

In the frame 60, a support plate 88 to which a rotation shaft driving motor 89 is attached is attached to the intermediate wall 69 of the first frame 61, and the rotation shaft driving motor 89 is attached to the support plate 88 while an output shaft 89a of the rotation shaft driving motor 89 is extended in the vertical direction.

An advancing and retracting shaft driving pulley 90 is attached to the output shaft 89a of the rotation shaft driving motor 89, an advancing and retracting shaft driven pulley 91 is attached to the advancing and retracting shaft 64 of the first frame 61, and the advancing and retracting shaft driving pulley 90 and the advancing and retracting shaft driven pulley 91 are interlocked by an advancing and retracting shaft timing belt 92. The advancing and retracting shaft driven pulley 91 is attached between the first bevel gear 83 provided on the advancing and retracting shaft 64 of the first frame 61 and the intermediate wall 69 of the first frame 61.

In the frame 60, the advancing and retracting shaft 64 of the first frame 61 is rotated by driving the rotation shaft driving motor 89 via the advancing and retracting shaft timing belt 92, and the advancing and retracting shaft 64 of the second frame 62 interlocked with the first frame 61 via the interlocking timing belt 87 is rotated similarly to the advancing and retracting shaft 64 of the first frame 61.

In the second frame 62 and the first frame 61 of the frame 60, pivot shafts 93, 94 are provided, respectively. Each of the pivot shafts 93, 94 protrudes outward from outer surfaces of the first side wall 65 and the second side wall 66, and is pivotally supported by bearings 95 provided at predetermined positions of a first support piece 72 and a second support piece 73 of the base 70. That is, the first frame 61 and the second frame 62 of the frame 60 are rotatable with respect to the base 70.

A frame driven pulley 96 is attached to the pivot shaft 94 provided on the side of the second side wall 66 of the first frame 61 while protruding outward from the first support piece 72 of the base 70.

The frame driven pulley 96 is interlocked with a frame driving pulley 98 attached to an output shaft 97 of a frame rotating motor 75 provided on the front side of the base end plate 71 of the base 70 via a rotation operation timing belt 99, and the first frame 61 is rotated by the frame rotating motor 75 while the second frame 62 connected to the first frame 61 via the connecting rods 63 is rotated.

The arm 50 includes an upper arm 51 for supporting the base end side of the puncture needle 40 and a lower arm 52 for supporting the leading end side of the puncture needle 40 with respect to the portion supported by the upper arm 51, and the puncture needle 40 can be attached thereto in parallel to the advancing and retracting shafts 64 of the frame 60.

The upper arm 51 is mainly constructed with a later-described upper connecting body 101 having a U-shape in plan view, an upper left intermediate piece 107, an upper left intermediate piece 108, a first sensor 111, and an upper leading end arm 120. The upper arm 51 supports the leading end side of the puncture needle 40 by way of a socket 53 (to be described later).

The lower arm 52 is mainly constructed with a later-described lower connecting body 103 having a U-shape in plan view, a lower left intermediate piece 109, a lower right intermediate piece 110, a second sensor 112, and a lower leading end arm 130. The lower arm 52 supports the leading end side of the puncture needle 40 with respect to the portion where the upper arm 51 supports the socket 53.

In particular, the substantially rectangular parallelepiped-shaped socket 53 that detachably fixes the puncture needle 40 is provided near the leading end of the upper arm 51 that supports the puncture needle 40 and at the leading end of the lower arm 52. The socket 53 can be detached from the upper arm 51 and the lower arm 52 with the upper arm 51 and the lower arm 52 opened to the right and left, and the socket 53 to which the puncture needle 40 is fixed can be detached from the arm 50 as necessary, which allows the puncture needle 40 to be quickly detached from the arm 50. That is, in the event that urgent removal of the puncture needle 40 is required while a patient is punctured with the puncture needle 40, the puncture needle 40 can manually be removed.

The shape of the socket is not limited to that of Embodiment 1, but may appropriately be decided according to shapes of various puncture needles.

The base end sides of the upper arm 51 and the lower arm 52 are attached to the frame 60. Specifically, an upper connecting body 101 that integrally connects an upper moving body 100 screwed onto the advancing and retracting shaft 64 of the first frame 61 of the frame 60 and an upper moving body 100 screwed onto the advancing and retracting shaft 64 of the second frame 62 is provided on the base end side of the upper arm 51, the upper connecting body 101 having a U-shape in plan view, and the base end side of the upper arm 51 is attached to the frame 60 via the upper connecting body 101. Similarly, a lower connecting body 103 that integrally connects a lower moving body 102 screwed onto the advancing and retracting shaft 64 of the first frame 61 of the frame 60 and a lower moving body 102 screwed onto the advancing and retracting shaft 64 of the second frame 62 is provided on the base end side of the lower arm 52, the lower connecting body 103 having a U-shape in plan view, and the base end side of the lower arm 52 is attached to the frame 60 via the lower connecting body 103.

The advancing and retracting shaft 64 and the upper moving body 100, and the advancing and retracting shaft 64 and the lower moving body 102 each constitute a ball screw mechanism, and the advancing and retracting shaft 64 of the first frame 61 and the advancing and retracting shaft 64 of the second frame 62 can be rotated by driving the rotation shaft driving motor 89 via the advancing and retracting shaft timing belt 92, which allows the positions of the upper moving body 100 and the lower moving body 102 to be changed on the advancing and retracting shaft 64. That is, by virtue of the ball screw mechanism, the rotation shaft driving motor 89 is driven to allow the upper arm 51 and the lower arm 52 to be advanced and retracted along the advancing and retracting shaft 64, which allows the puncture needle 40 to be moved in a puncture direction to perform the puncture.

The upper connecting body 101 and the lower connecting body 103 have the same structure, and the upper connecting body 101 will be described as a representative.

The upper connecting body 101 is integrally formed by a left frame 104 attached onto the side of the left side surface of the upper moving body 100 screwed onto the advancing and retracting shaft 64 of each of the first frame 61 and the second frame 62, a right frame 105 attached onto the side of the right side surface of the upper moving body 100 screwed onto the advancing and retracting shaft 64 of each of the first frame 61 and the second frame 62, and a connecting frame 106 connecting the rear ends of the left frame 104 and the right frame 105. The upper connecting body 101 includes coupling pieces 104a, 105a being the end edges of the left frame 104 and the right frame 105, respectively, on the side of puncture needle 40, the end edges protruding toward the side of the puncture needle 40. In Embodiment 1, the left frame 104 and each upper moving body 100 are connected with an appropriate bearing interposed therebetween, and the right frame 105 and each upper moving body 100 are also connected with an appropriate bearing interposed therebetween.

A linear guide is attached to the second frame 62. That is, as illustrated in FIG. 3, a flat linear guide disposition unit 62a protruding forward is provided on the front side of the second frame 62, a linear guide rail 62b is disposed in the rear surface of the linear guide disposition unit 62a in parallel to the advancing and retracting shaft 64, and a slider 62c that slides along the linear guide rail 62b is integrally connected to the upper moving body 100 and the lower moving body 102. Consequently, the upper moving body 100 and the lower moving body 102 can be moved in parallel to the advancing and retracting shaft 64 in a stable orbit, and vibrations of the upper moving body 100 and the lower moving body 102 moving along the advancing and retracting shaft 64 can be prevented.

The upper arm 51 connects an upper left intermediate piece 107 having a predetermined length to the coupling piece 104a of the left frame 104 of the upper connecting body 101, and connects an upper right intermediate piece 108 having a predetermined length to the coupling piece 105a of the right frame 105 of the upper connecting body 101.

In particular, the upper left intermediate piece 107 and the upper right intermediate piece 108 are bent into a crank shape, thereby bending the upper arm 51 to offset the puncture needle 40 in the puncture direction.

Similarly, the lower arm 52 connects a lower left intermediate piece 109 having a predetermined length to the coupling piece 104a of the left frame 104 of the lower connecting body 103, and connects a lower right intermediate piece 110 having a predetermined length to the coupling piece 105a of the right frame 105 of the lower connecting body 103.

In particular, the lower left intermediate piece 109 and the lower right intermediate piece 110 are bent into a crank shape, thereby bending the lower arm 52 to offset the puncture needle 40 in the puncture direction.

Thus, the upper arm 51 and the lower arm 52 are bent in the crank shape to offset the puncture needle 40 in the puncture direction, which allows the patient to be punctured with the puncture needle 40 without bringing the frame 60 and the base 70 of the puncture unit 30 into contact with the patient.

A first sensor 111 constructed with a six-axis force sensor is provided in a middle of the upper arm 51. Similarly, a second sensor 112 constructed with a six-axis force sensor is provided in the middle of the lower arm 52. Specifically, the upper left intermediate piece 107 and the upper right intermediate piece 108 are integrally connected to a holding plate holding the rear end side of the first sensor 111, and connected to the upper leading end arm 120 with the first sensor 111 interposed therebetween. The lower left intermediate piece 109 and the lower right intermediate piece 110 are integrally connected to a holding plate holding the rear end side of the second sensor 112, and connected to the lower leading end arm 130 with the second sensor 112 interposed therebetween.

In particular, the first sensor 111 and the second sensor 112 are provided at the same position in the vertical direction in an initial posture in which the frame 60 is not inclined. The first sensor 111 and the second sensor 112 detect stresses generated in the upper arm 51 and the lower arm 52, and interrupt the puncture in the case that a detected amount exceeds a predetermined threshold. The first sensor 111 and the second sensor 112 are electrically connected to a control device (to be described later).

The first sensor 111 and the second sensor 112 are preferably disposed at positions that do not fall under the CT gantry in the arm 50 in order to prevent artifact generation caused by a metal member during work in the vicinity of the CT gantry. In addition, in order to accurately detect the stress generated in the puncture needle 40 through the upper arm 51 and the lower arm 52, preferably the first sensor 111 and the second sensor 112 are disposed as close to the puncture needle 40 as possible.

The upper leading end arm 120 includes a base 121 connected to the front side of the first sensor 111, a pair of left and right upper arm pieces 122, 122 extending forward from the left and right ends of the base 121, and a socket grip 123. The upper leading end arm 120 including a clamp screw 127 and the like is made of a resin material. The pair of upper arm pieces 122, 122 is bent in the crank shape, thereby bending the upper arm 51 to offset the puncture needle 40 in the puncture direction. The rear ends of the pair of upper arm pieces 122, 122 are pivotally supported at the left and right ends of the base 121, and each of the leading end sides of the upper arm pieces 122, 122 can be opened in a horizontal direction. A pair of upper connecting arm pieces 124, 124, which extends from opposing surfaces of the upper arm pieces 122, 122 and connects the upper arm pieces 122, 122 is provided in the vicinity of the leading ends of the pair of upper arm pieces 122, 122. The upper arm pieces 122, 122 are fixed by the clamp screw 127 while leading ends of the upper arm pieces 122, 122 are locked in each other, thereby integrally connecting the upper arm pieces 122, 122.

The socket grip 123 includes socket holding arm pieces 125, 125 provided near the rear end sides of the upper connecting arm pieces 124, 124, the socket holding arm pieces 125, 125 being extended from opposing surfaces of the upper arm pieces 122, 122 to support the left and right side surfaces of the socket 53. The leading ends of the socket holding arm pieces 125, 125 include engagement protrusions 126, 126 engaged with engagement recesses 53*a*, 53*a* drilled in the upper sides of the left and right side surfaces of the socket 53. In the socket holding arm pieces 125, 125, the engagement protrusions 126, 126 are engaged with the engagement recesses 53*a*, 53*a*, and the socket 53 is rotatably held with respect to the socket holding arm pieces 125, 125, and the base end side of the socket 53 is gripped. When the clamp screw 127 is removed to open the leading ends of the upper arm pieces 122, 122 to the right and left, the engagement protrusions 126, 126 of the socket holding arm pieces 125, 125 are disengaged from the engagement recesses 53*a*, 53*a* to release the state in which the base end side of the socket 53 is gripped.

The lower leading end arm 130 includes a base 131 connected to the front side of the second sensor 112, a pair of left and right lower arm pieces 132, 132 horizontally extending forward from the left and right ends of the base 131, and a socket grip 133. The lower leading end arm 130 including a clamp screw 137 and the like is made of a resin material. The rear ends of the pair of lower arm pieces 132, 132 are pivotally supported at the left and right ends of the base 131, and the leading end sides of the lower arm pieces 132, 132 can horizontally be opened. A pair of lower connecting arm pieces 134, 134, which extends from the opposing surfaces of the lower arm pieces 132, 132 and connects the lower arm pieces 132, 132, is provided in the vicinity of the leading ends of the pair of lower arm pieces 132, 132. The lower arm pieces 132, 132 are fixed by the clamp screw 137 while leading ends of the lower arm pieces 132, 132 are locked in each other, thereby integrally connecting the lower arm pieces 132, 132.

The socket grip 133 includes socket holding arm pieces 135, 135 provided at the leading ends of the lower arm piece 132, 132, the socket holding arm pieces 135, 135 being extended from the opposing surfaces of the lower arm pieces 132, 132 to support the left and right side surfaces of the socket 53. The leading ends of the socket holding arm pieces 135, 135 include engagement protrusions 136, 136 engaged with engagement recesses 53*b*, 53*b* drilled in the lower sides of the left and right side surfaces of the socket 53. In the socket holding arm pieces 135, 135, the engagement protrusions 136, 136 are engaged with the engagement recesses 53*b*, 53*b*, and the socket 53 is rotatably held with respect to the socket holding arm pieces 135, 135, and the leading end side of the socket 53 is gripped. When the clamp screw 137 is removed to open the leading ends of the lower arm pieces 132, 132 to the right and left, the engagement protrusions 136, 136 of the socket holding arm pieces 135, 135 are disengaged from the engagement recesses 53*b*, 53*b* to release the state in which the base end side of the socket 53 is gripped.

The socket 53 has a substantially rectangular parallelepiped shape, and is made of a resin material. The socket 53 can be divided into left and right parts at the center in the crosswise direction, and a fitting hole in which the base end of the puncture needle 40 is fitted is made in the inner surface of the socket 53. In the socket 53, while the base end of the puncture needle 40 is fitted in the fitting hole, the engagement protrusions 126, 126 of the socket holding arm pieces 125, 125 are engaged with the engagement recesses 53*a*, 53*a*, and the engagement protrusions 136, 136 of the socket holding arm pieces 135, 135 are engaged with the engagement recesses 53*b*, 53*b*, thereby holding the base end side of the puncture needle 40.

The puncture needle 40 is a biopsy needle used to puncture a subject under X-ray fluoroscopy by CT to collect and examine a tissue. The puncture needle 40 includes an inner needle having a hook-shaped leading end and a tubular needle tube in which the inner needle is accommodated. The puncture needle 40 collects the tissue by taking in and out the inner needle from the leading end of the needle tube.

The puncture needle is not limited to that of Embodiment 1, but a puncture needle for other purposes such as a radiofrequency therapy puncture needle may be used as the puncture needle.

The upper arm 51 and the lower arm 52 can also be configured such that a distance between the frame 60 and the puncture needle 40 is lengthened by interposing an extending member in the middle as necessary.

The puncture robot 1 includes a control device (for example, a Personal Computer (PC)) that controls the puncture robot 1 in the robot body 10. Each actuator in the robot body 10, the rotation shaft driving motor 89 that rotates the advancing and retracting shaft 64 provided in the frame 60 of the puncture unit 30, and the frame rotating motor 75 that rotates the first frame 61 provided in the base 70 of the puncture unit 30 can be operated by the control device. A worker who performs puncture work issues an operation instruction using an operation tool (controller) electrically connected to the PC, whereby the puncture robot 1 is operated according to the operation instruction. The control device of the puncture robot 1 acquires detection signals of the first sensor 111 and the second sensor 112, and can measure puncture force when puncturing the subject with the puncture needle 40.

In the puncture robot 1 having the above configuration, the puncture unit 30 can be moved to a desired position by driving the robot body 10. Consequently, the puncture position of the puncture needle 40 can be adjusted. The puncture unit 30 can rotate with the connecting rod 13 as the rotation shaft by driving the connecting rod actuator of the robot body 10. Using the frame rotating motor 75 that rotates the first frame 61 provided in the base 70 of the puncture unit 30, posture changing motion can be performed in the biaxial direction of the puncture needle 40, and a puncture angle of the puncture needle 40 can be adjusted.

Specifically, in the puncture robot 1, the frame 60 swings about the pivot shaft 94 by driving the frame rotating motor 75, the frame 60 is inclined, and the socket 53 holding the puncture needle 40 rotates by the operations of the upper arm 51 and the lower arm 52, which are linked with each other via the frame 60, and the puncture needle 40 is inclined at the same angle as the angle at which the frame 60 is inclined. That is, the posture of the puncture needle 40 can be changed with the needle shaft on the base end side of the puncture needle 40 as the rotation center. Thus, for example, the posture of the puncture needle 40 can be changed in the small space in the CT gantry, and the operability of the puncture robot 1 is improved.

In the puncture robot 1 of Embodiment 1, the rotation shaft driving motor 89 that advances and retracts the puncture needle 40 and the frame rotating motor 75 that changes the rotation center of the posture of the puncture needle 40 are disposed behind the frame 60. This enables the rotation shaft driving motor 89 and the frame rotating motor 75 to be arranged outside the CT gantry during the puncture work under X-ray fluoroscopy by CT. Thus, these driving motors do not affect the CT image, but operability of the puncture robot 1 is improved.

In the puncture robot 1 of Embodiment 1, a portion (excluding the puncture needle 40) constituting the front side (the side of the puncture needle 40) with respect to the first sensor 111 and the second sensor 112 in the upper arm 51 and the lower arm 52 is formed of a resin material. Consequently, the metallic material except for the puncture needle 40 can be prevented from entering the CT gantry during the puncture work under the X-ray fluoroscopy by CT, and the artifact generation can be prevented, so that the puncture work can accurately be performed.

In the puncture robot 1 of Embodiment 1, the puncture operation of the puncture needle 40 is performed by the rotation shaft driving motor 89, the operation to change the inclination of the puncture needle 40 is performed by the frame rotating motor 75, and these operations can independently be performed.

In the puncture robot 1 of Embodiment 1, the first sensor 111 constructed with the six-axis force sensor is provided in the middle of the upper arm 51, and the second sensor 112 constructed with the six-axis force sensor is provided in the middle of the lower arm 52. Consequently, the detection signals of the first sensor 111 and the second sensor 112 can be acquired to measure the puncture force when the subject is punctured with the puncture needle 40. The first sensor 111 and the second sensor 112, which measure the force during puncture, can be disposed as close to the puncture needle 40 as possible and outside the CT gantry. As a result, it can be applied to design of an interface for monitoring a puncture state and presenting the puncture force to a practitioner to improve remote operability.

In the puncture robot 1 of Embodiment 1, the upper arm 51 and the lower arm 52 are bent into the crank shape to offset the puncture needle 40 in the puncture direction. Thus, a movable range of the puncture needle 40 is set below the movable ranges of the upper moving body 100 and the lower moving body 100 on the advancing and retracting shaft 64, so that the puncture can be performed using even a root of the puncture needle 40.

In the puncture robot 1 of Embodiment 1, the puncture work can be performed in the vicinity of the gantry of CT irradiating X-rays instead of the practitioner, and X-ray exposure of the practitioner can be prevented.

In the puncture robot 1 of Embodiment 1, by disposing the linear guide in the frame 60, the puncture needle 40 can be moved in the puncture direction as soon as possible while the vibration generated in the puncture needle 40 is prevented. This enables the accuracy to be improved in the puncture operation.

Embodiment 2

A puncture robot 1A according to Embodiment 2 will be described below with reference to the drawings.

Figure 7:
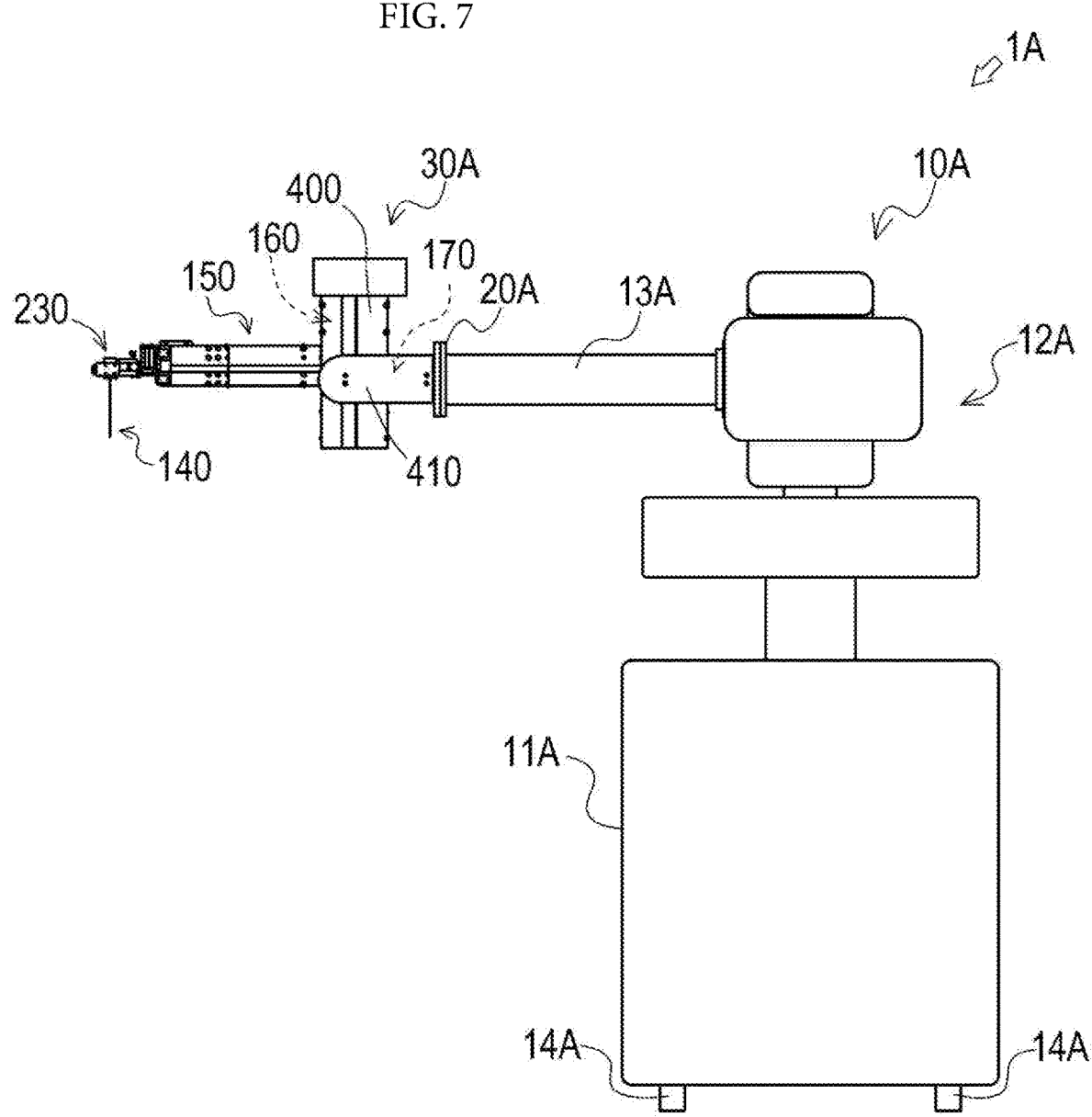
FIG. 7 is a side view illustrating a puncture robot according Embodiment 2 of the present invention.
Figure 8:
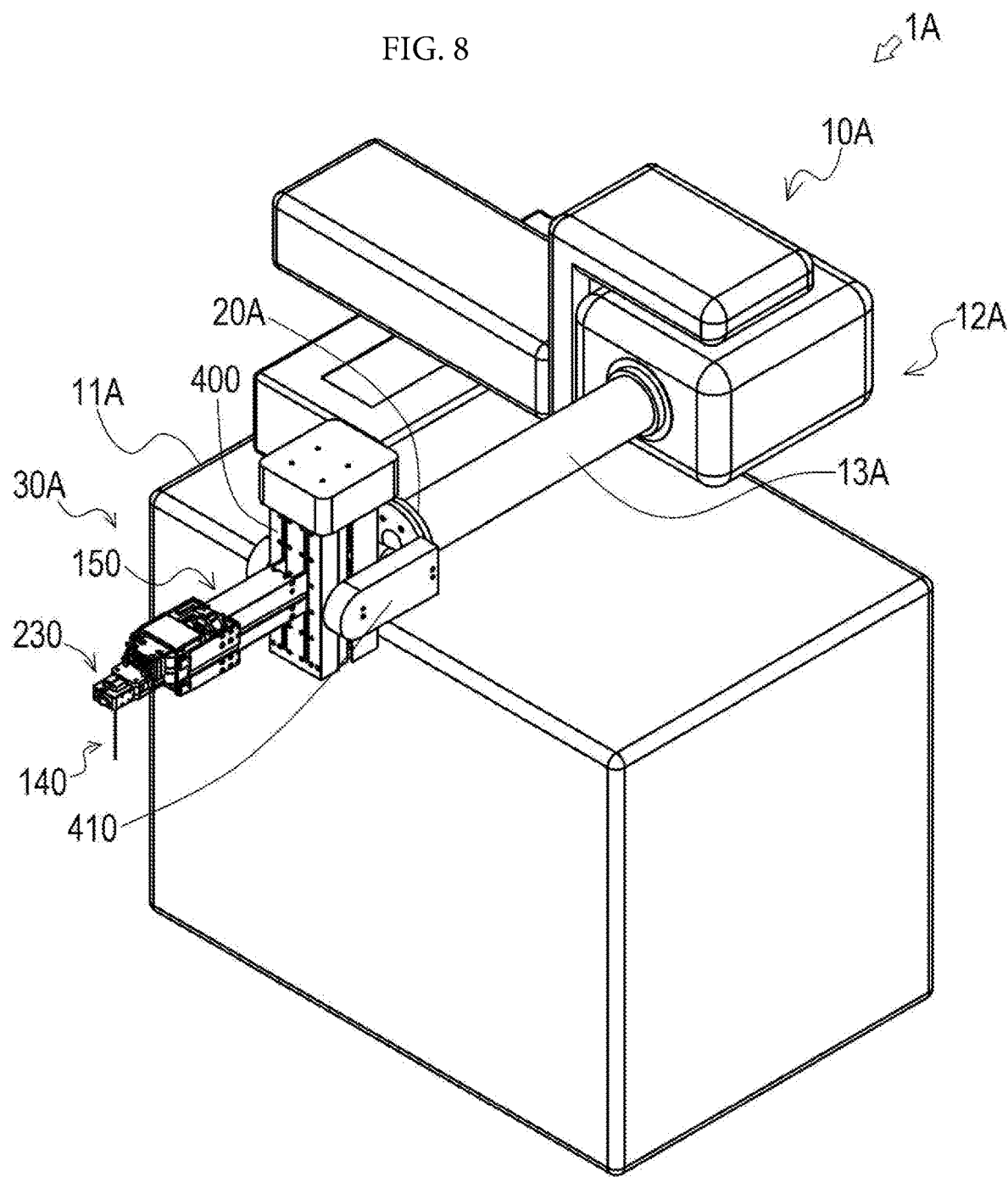
FIG. 8 is a perspective view illustrating the puncture robot of Embodiment 2.

As illustrated in FIG. 7 and FIG. 8, the puncture robot 1A according to Embodiment 2 includes a robot body 10A and a puncture unit 30A attached to the moving end 20A of the robot body 10A. The puncture unit 30A is a portion constituting an instrument of the robot body 10A.

The robot body 10A includes a casing 11A having a rectangular parallelepiped shape, a driver 12A disposed above the casing 11A, and a connecting rod 13A horizontally attached to one end of the driver 12A, a leading end side of the connecting rod 13A extending to an outside of the casing 11A. The casing 11A is electrically connected to a second casing (not illustrated) in which the control device is accommodated by wiring. The robot body 10A includes a handle (not illustrated) provided at an upper end of a side surface of the casing 11A and a plurality of casters 14A provided in a bottom portion of the casing 11A, and a user grips the handle to freely move the robot body 10A. The driver 12A moves a flange-shaped moving end 20A provided at the leading end of the connecting rod 13A using a plurality of actuators (not illustrated) in three dimensions of the advancing and retracting direction, the vertical direction (elevation direction), and the crosswise direction. In the robot body 10A, the moving end 20A is moved in the advancing and retracting direction, the vertical direction, and the crosswise direction by a linear motion joint. The driver 12A can rotate the connecting rod 13A about an axis of the connecting rod 13A by an actuator (not illustrated). The robot body 10A drives the driver 12A to move the puncture unit 30A attached to the moving end 20A provided at the leading end of the connecting rod 13A to a desired position. The robot body 10A moves the puncture unit 30A in the advancing and retracting direction, the vertical direction, and the crosswise direction by operating the linear motion joint, whereby the puncture unit 30A can be moved in the stable orbit even in the small space such as the vicinity of the CT gantry.

A puncture unit 30A is attached to the moving end 20A disposed at the leading end of the connecting rod 13A.

Figure 9:
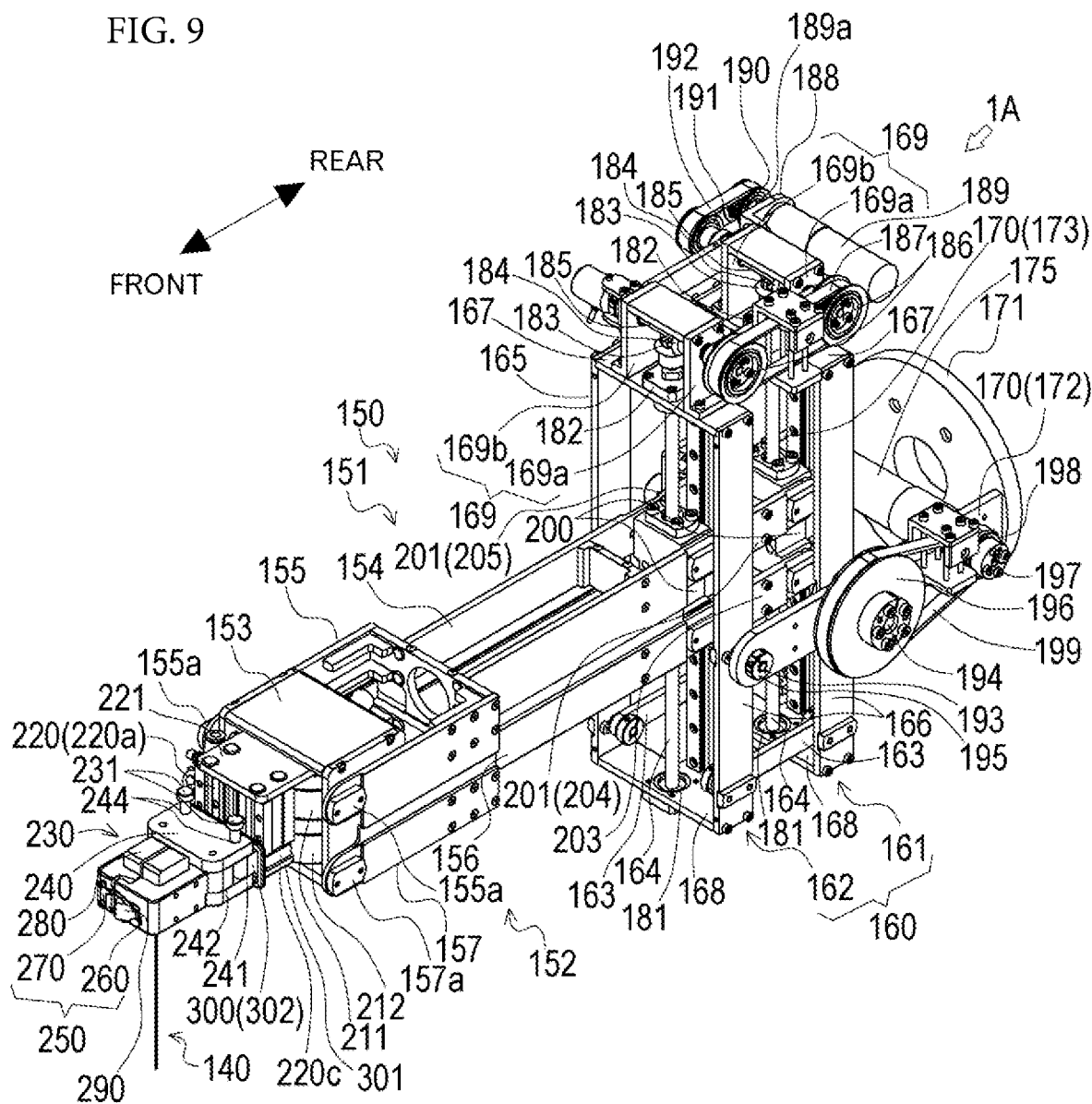
FIG. 9 is a perspective view illustrating a puncture unit (in a state in which a frame cover is removed) of Embodiment 2.

In the puncture unit 30A, it is assumed that a direction of a double-headed arrow in FIG. 9 is the front-back direction.

As illustrated in FIG. 7 and FIG. 8, the puncture unit 30A includes an arm 150 the leading end of which has a puncture needle 140 attached thereto, a frame 160 (see FIG. 9) to which the base end of the arm 150 is attached, a base 170 (see FIG. 9) that supports the frame 160, a frame cover 400 that covers the frame 160, a base cover 410 that covers the base 170. The puncture unit 30A is fixedly attached to the moving end 20A of the connecting rod 13A via the base 170.

Thus, when the connecting rod 13A is rotated about the axis by a connecting rod rotating actuator (not illustrated) included in the robot body 10A, the puncture unit 30A rotates with the connecting rod 13A as the rotation shaft.

FIG. 9 illustrates the state in which the frame cover 400 and the base cover 410 are removed in order to illustrate the detailed structure of the puncture unit 30A.

The base 170 includes a disk-shaped base end plate 171 to which the moving end 20A at the leading end of the connecting rod 13A is attached and a flat first support piece 172 and a flat second support piece 173, which extend forward from both left and right ends of a base end plate 171 to movably support the frame 160. The base 170 has a substantially U-shape in plan view.

A guide 174 to which the leading end of the connecting rod 13 is attached is provided on a rear side of the base end plate 171. The positioning is performed by attaching the leading end of the connecting rod 13A to the guide 174, and a clamp screw is screwed from a rear end face of the flange-shaped moving end 20A to fix the puncture unit 30A to the leading end of the moving end 20A.

A frame rotating motor 175 that rotates the frame 160 is attached to a front side of the base end plate 171 as described later.

The frame 160 includes a first frame 161, a second frame 162, and a plurality of connecting rods 163. Each of the first frame 161 and the second frame 162 has a rectangular frame shape, and an advancing and retracting shaft 164 (for example, a threaded shaft of a ball screw) extending in the vertical direction is provided inside each of the first frame 161 and the second frame 162. The plurality of connecting rods 163 connect the first frame 161 and the second frame 162 while the first frame 161 and the second frame 162 face each other. In particular, a parallel link is formed by connecting the first frame 161 and the second frame 162 using the connecting rods 163.

The first frame 161 and the second frame 162 have the same structure, and the first frame 161 will be described below as a representative.

The first frame 161 includes a first side wall 165, a second side wall 166, a third side wall 167, and a fourth side wall 168. The first side wall 165 and the second side wall 166 have a flat plate shape, and extend in the vertical direction while facing each other. The third side wall 167 has a flat plate shape, and connects upper end edges of the first side wall 165 and the second side wall 166. The fourth side wall 168 has a flat plate shape, and connects lower end edges of the first side wall 165 and the second side wall 166. The first frame 161 is formed into a vertically elongated rectangular frame shape.

A lower bearing 181 and an upper bearing 182, which support the advancing and retracting shaft 164 extending in the vertical direction in parallel with the first side wall 165 and the second side wall 166, are provided in the fourth side wall 168 and the third side wall 167, respectively, and the advancing and retracting shaft 164 is pivotally supported by the lower bearing 181 and the upper bearing 182.

The advancing and retracting shaft 164 extends so as to protrude upward from the upper bearing 182, and a first bevel gear 183 is attached to the upper end of the upwardly protruding advancing and retracting shaft 164.

The frame 160 includes an upper frame 169, which has a rectangular shape in side view so as to surround the first bevel gear 183, in the upper portion of the third side wall 167.

A second bevel gear 184 engaging with the first bevel gear 183 is attached to a rotation shaft 185 rotatably mounted on a first upper side wall 169a and a second upper side wall 169b of the upper frame 169 above the first bevel gear 183.

An end of the rotation shaft 185 on the side of the first upper side wall 169a extends so as to protrude outward, and an interlocking pulley 186 is attached to one end of the protruding rotation shaft 185. The interlocking pulley 186 of the first frame 161 and the interlocking pulley 186 of the second frame 162 have the same shape, and are interlocked with each other via an interlocking timing belt 187.

In the frame 160, a support plate 188 to which a rotation shaft driving motor 189 is attached is attached to the second upper side wall 169b of the upper frame 169, and a rotation shaft driving motor 189 is attached to the support plate 188 while an output shaft 189a of the rotation shaft driving motor 189 is extended in the horizontal direction.

An advancing and retracting shaft driving pulley 190 is attached to the output shaft 189a of the rotation shaft driving motor 189, an advancing and retracting shaft driven pulley 191 is attached to the advancing and retracting shaft 164 of the first frame 161, and the advancing and retracting shaft driving pulley 190 and the advancing and retracting shaft driven pulley 191 are interlocked by an advancing and retracting shaft timing belt 192. The advancing and retracting shaft driven pulley 191 is attached to the other end of the rotation shaft 185.

In the frame 160, the advancing and retracting shaft 164 of the first frame 161 is rotated by driving the rotation shaft driving motor 189 via the advancing and retracting shaft timing belt 192, and the advancing and retracting shaft 164 of the second frame 162 interlocked with the first frame 161 via the interlocking timing belt 187 is rotated similarly to the advancing and retracting shaft 164 of the first frame 161.

In the second frame 162 and the first frame 161 of the frame 160, pivot shafts 193, 194 are provided, respectively. Each of the pivot shafts 193, 194 protrudes outward from outer surfaces of the first side wall 165 and the second side wall 166, and is pivotally supported by bearings 195 provided at predetermined positions of a first support piece 172 and a second support piece 173 of the base 170. That is, the first frame 161 and the second frame 162 of the frame 160 are rotatable with respect to the base 170.

A frame driven pulley 196 is attached to the pivot shaft 194 provided on the side of the second side wall 166 of the first frame 161 while protruding outward from the first support piece 172 of the base 170.

The frame driven pulley 196 is interlocked with a frame driving pulley 198 attached to an output shaft 197 of a frame rotating motor 175 provided on the front side of the base end plate 171 of the base 170 via a rotation operation timing belt 199, and the first frame 161 is rotated by the frame rotating motor 175 while the second frame 162 connected to the first frame 161 via the connecting rods 163 is rotated.

The arm 150 supports a sensor holder 153, which has a rectangular tubular shape and holds a sensor, at the leading end of the arm 150. The arm 150 includes an upper arm 151 supporting the front upper end side of the sensor holder 153, a lower arm 152 supporting the front lower end side of the sensor holder 153, the sensor holder 153, an air cylinder 220, and a needle grip 230.

The upper arm 151 is mainly constructed with an upper arm base 154 having a rectangular shape in plan view and an upper arm leading end 155 having a U-shape in plan view, the upper arm leading end 155 being connected to the front end of the upper arm base 154. A pair of left and right pivot supports 155a by which the front upper end side of the sensor holder 153 is pivotally supported is provided at the leading end of the upper arm leading end 155.

The lower arm 152 is mainly constructed with a lower arm base 156 having a rectangular shape in plan view and a lower arm leading end 157 having a U-shape in plan view, the lower arm leading end 157 being connected to the front end of the lower arm base 156. A pair of left and right pivot supports 157a by which the front lower end side of the sensor holder 153 is pivotally supported is provided at the leading end of the lower arm leading end 157.

The base end sides of the upper arm 151 and the lower arm 152 are attached to the frame 160. Specifically, an upper connecting body 201 that integrally connects an upper portion of a vertically long first moving body 200 screwed onto the advancing and retracting shaft 164 of the first frame 161 of the frame 160 and an upper portion of a vertically long second moving body 200 screwed onto the advancing and retracting shaft 164 of the second frame 162 is provided on the base end side of the upper arm 151, and the base end side of the upper arm 151 is attached to the frame 160 via the upper connecting body 201. Similarly, a lower connecting body 203 that integrally connects a lower portion of the first moving body 200 screwed onto the advancing and retracting shaft 164 of the first frame 161 of the frame 160 and a lower portion of the second moving body 200 screwed onto the advancing and retracting shaft 164 of the second frame 162 is provided on the base end side of the lower arm 152, and the base end side of the lower arm 152 is attached to the frame 160 via the lower connecting body 203.

The advancing and retracting shaft 164 of the first frame 161 and the first moving body 200, and the advancing and retracting shaft 164 of the second frame 162 and the second moving body 200 each constitute a ball screw mechanism, and the advancing and retracting shaft 164 of the first frame 161 and the advancing and retracting shaft 164 of the second frame 162 can be rotated by driving the rotation shaft driving motor 189 via the advancing and retracting shaft timing belt 192, which allows the positions of the first moving body 200 and the second moving body 200 to be changed on the advancing and retracting shaft 164. That is, by virtue of the ball screw mechanism, the rotation shaft driving motor 189 is driven to allow the upper arm 151 and the lower arm 152 to be advanced and retracted along the advancing and retracting shaft 164, which allows the puncture needle 140 to be moved in the puncture direction to perform the puncture.

The upper connecting body 201 and the lower connecting body 203 have the same structure, and the upper connecting body 201 will be described as a representative.

The upper connecting body 201 is formed by a left frame 204 attached onto the side of the left side surface of the first moving body 200 screwed onto the advancing and retracting shaft 164 of the first frame 161 and the side of the left side surface of the second moving body 200 screwed onto the advancing and retracting shaft 164 of the second frame 162 and a right frame 205 attached onto the side of the right side surface of the first moving body 200 screwed onto the advancing and retracting shaft 164 of the first frame 161 and the side of the right side surface of the second moving body 200 screwed onto the advancing and retracting shaft 164 of the second frame 162. In Embodiment 2, the left frame 204, the first moving body 200, and the second moving body 200 are connected with appropriate bearings interposed therebetween, and the right frame 205, the first moving body 200, and the second moving body 200 are also connected with appropriate bearings interposed therebetween.

Figure 10:
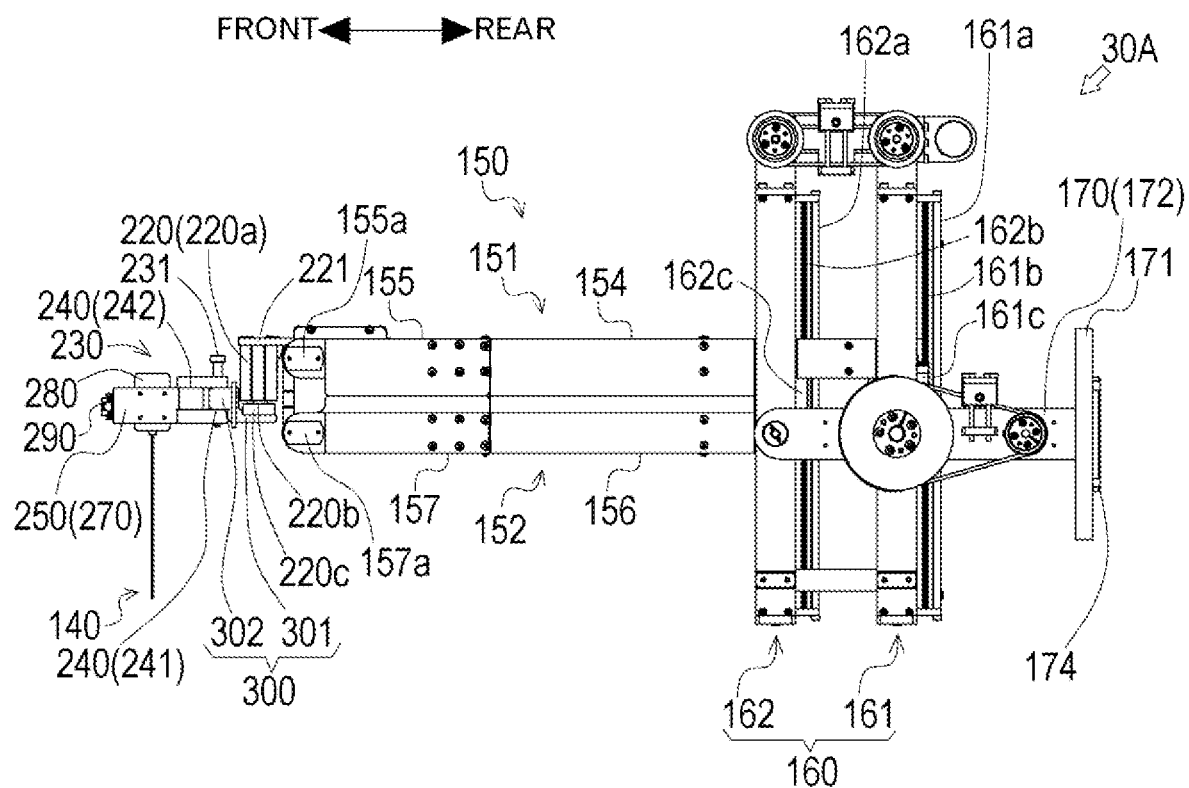
FIG. 10 is a side view illustrating the puncture unit (in the state in which the frame cover is removed) of Example 2.
Figure 11:
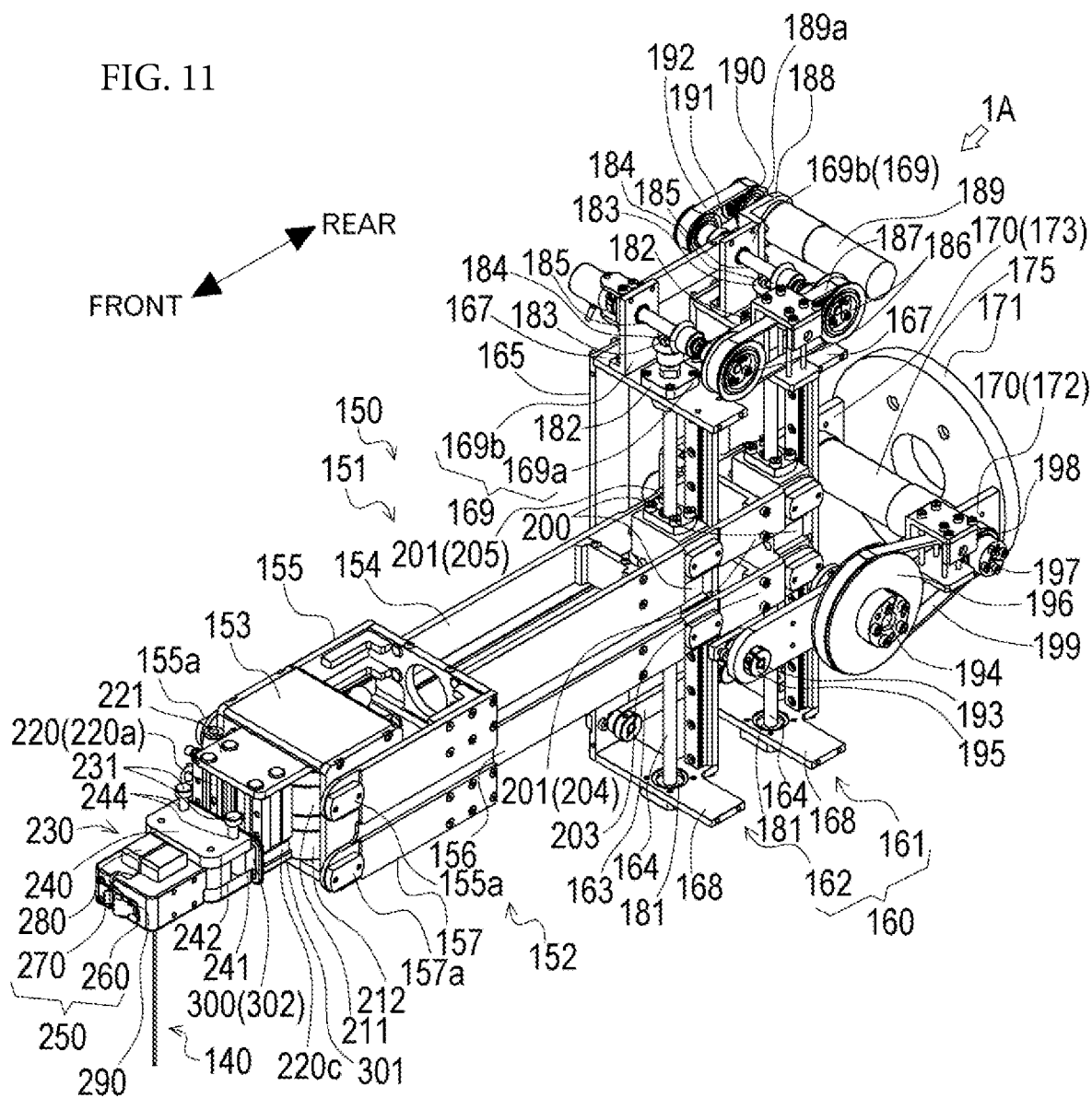
FIG. 11 is a side view illustrating the puncture unit (in the state in which the frame cover and the second side walls of the first frame and the second frame are removed) of Embodiment 2.

Linear guides are attached to the first frame 161 and the second frame 162. That is, as illustrated in FIG. 10, the rear sides of the first frame 161 and the second frame 162 include flat linear guide disposition units 161a, 162a protruding rearwardly, respectively, and linear guide rails 161b, 162b are disposed in the front surfaces of the linear guide disposition units 161a, 162a in parallel to the advancing and retracting shafts 164, and sliders 161c, 162c that slide along the rails 161b, 162b are integrally connected to the first moving body 200 and the second moving body 200. Consequently, the first moving body 200 and the second moving body 200 can be moved in parallel to the advancing and retracting shaft 164 in the stable orbit, and the vibrations of the first moving body 200 and the second moving body 200 moving along the advancing and retracting shaft 164 can be prevented.

An upper sensor 211 and a lower sensor 212, which are six-axis force sensors, are disposed in the sensor holder 153 while vertically stacked. The lower sensor 212 is fixed to the bottom inside the sensor holder 153, and the upper sensor 211 is connected to the lower sensor 212 while placed on the upper portion of the lower sensor 212. One end of a support plate 221 supporting the air cylinder 220 is fixed to the upper end surface of the upper sensor 211. A predetermined gap is provided between the support plate 221 and a ceiling surface inside the sensor holder 153. The other end of the support plate 221 extends to the outside of the sensor holder 153 and protrudes forward. One end side (the upper end side in FIG. 10) of an air cylinder body 220a that is a main portion of the air cylinder 220 is connected to the lower surface at the other end of the support plate 221. The upper sensor 211 and the lower sensor 212 are connected to the needle grip 230 with the support plate 221 and the air cylinder 220 interposed therebetween.

The air cylinder 220 has a substantially rectangular parallelepiped outer shape and is a pneumatically driven linear actuator. The air cylinder 220 includes the air cylinder body 220a that is the main portion of the air cylinder 220, a piston rod 220b (see FIG. 10), which is accommodated in the air cylinder body 220a to advance and retract with a predetermined stroke, and a plate-shaped blade 220c attached to the leading end of the piston rod 220b. In the air cylinder 220, the blade 220c instantaneously moves forward and backward (forward at puncture) with a predetermined stroke along the advancing and retracting direction of the piston rod 220b (the vertical direction in the state of FIG. 10) by the air pressure of the supplied air.

The upper sensor 211 and the lower sensor 212 detect stress generated in the needle grip 230 through the support plate 221 and the air cylinder 220, and stop the puncture when the detected amount exceeds a predetermined threshold. The upper sensor 211 and the lower sensor 212 are electrically connected to the control device (to be described later). The upper sensor 211 and the lower sensor 212 are connected in series while vertically connected to each other. In the above configuration, the upper sensor 211 and the lower sensor 212 can simultaneously detect the stress generated in the needle grip 230. Even if one of the upper sensor 211 and the lower sensor 212 fails, the stress generated in the needle grip 230 can be detected by the other sensor. Consequently, the stress can be detected without interruption, and the safety is enhanced during the puncture operation.

The upper sensor 211 and the lower sensor 212 are preferably disposed at positions that do not fall under the CT gantry in the arm 150 in order to prevent artifact generation caused by a metal member during work in the vicinity of the CT gantry. In addition, in order to accurately detect the stress generated in the puncture needle 140 through the upper arm 151 and the lower arm 152, preferably the upper sensor 211 and the lower sensor 212 are disposed as close to the puncture needle 140 as possible.

The needle grip 230 is attached to the blade 220c of the air cylinder 220 with an air cylinder fixture 300 interposed therebetween, the air cylinder fixture 300 being a fixing jig that fixes the needle grip 230 to the air cylinder 220. The air cylinder fixture 300 includes a plate-shaped abutment fixing unit 301 that is fixed by abutting on the surface (the lower surface in the state of FIG. 10) of the blade 220c and a fitting unit 302 having a substantially rectangular parallelepiped shape, the fitting unit 302 being formed into a shape protruding on the front side in adjacent to the abutment fixing unit 301, and fitted in a fitted unit 241 of the needle grip 230 (the needle grip arm fixture 240). Through-holes in which later-described fixing pins 231 can be inserted are provided in the fitting unit 302.

The needle grip 230 includes the needle grip arm fixture 240, a pair of needle grip arms 250, and a plurality of (two in Embodiment 2) fixing pins 231.

The needle grip arm fixture 240 is a resin member having an H-shape in side view, and includes the fitted unit 241, which is provided on the rear end side and in which the fitting unit 302 of the air cylinder fixture 300 is fitted, a rotation support 242 that pivotally supports the base end side of each of the pair of needle grip arms 250 (the left needle grip arm 260 and the right needle grip arm 270) on the front end side, and a plurality of through-holes 244 penetrating the fitted unit 241 in the vertical direction. While the fitting unit 302 of the air cylinder fixture 300 is fitted in the fitted unit 241, the fixing pins 231 are inserted, and the needle grip arm fixture 240 is attached to the air cylinder fixture 300. Consequently, by inserting or removing the fixing pins 231, the needle grip arm fixture 240 can easily be attached to and detached from the air cylinder fixture 300 attached to the air cylinder 220.

The needle grip arm 250 mainly includes a pair of left needle grip arm 260 and right needle grip arm 270 extending forward and a puncture needle holder 280 holding the base end of the puncture needle 140. The left needle grip arm 260, the right needle grip arm 270, and the puncture needle holder 280 are made of a resin material. The rear ends of the pair of left needle grip arm 260 and right needle grip arm 270 are pivotally supported at the left and right ends of the rotation support 242 of the needle grip arm fixture 240, and the left needle grip arm 260 and the right needle grip arm 270 can be opened by rotating the leading end sides of the left needle grip arm 260 and the right needle grip arm 270 within a range of 90 degrees in the left and right horizontal directions. The puncture needle holder 280 has a substantially rectangular parallelepiped shape, and is laterally divided at the center in the crosswise direction, and is attached to opposing recesses of the right needle grip arm 270 and the puncture needle holder 280 using attachment members. A fitting hole in which the base end of the puncture needle 140 is fitted is made in the inner surface of the puncture needle holder 280. The puncture needle holder 280 can be divided into the right and left parts by opening and closing the left needle grip arm 260 and the right needle grip arm 270, and the base end of the puncture needle 140 can detachably be engaged using the fitting hole. A snap lock 290 is provided at the front ends of the left needle grip arm 260 and the right needle grip arm 270. The left needle grip arm 260 and the right needle grip arm 270 are closed in the state in which the base end of the puncture needle 140 is fitted in the fitting hole and in the state in which the opposing inside surfaces of the left needle grip arm 260 and the right needle grip arm 270 abut on each other, and the base end side of the puncture needle 140 is held by fastening the snap lock 290.

The shape of the puncture needle holder 280 is not limited to that of Embodiment 2, but may appropriately be decided according to shapes of various puncture needles. The puncture needle holder 280 may be formed not separately from the left needle grip arm 260 and the right needle grip arm 270, but integrally with the left needle grip arm 260 and the right needle grip arm 270.

The puncture needle 140 is detachable from the left needle grip arm 260 and the right needle grip arm 270 by releasing the snap lock 290 to open the left needle grip arm 260 and the right needle grip arm 270 to the right and left, and the puncture needle 140 can quickly be removed from the needle grip arm 250 as necessary. That is, the puncture needle 140 can manually be pulled out in the case that the necessity of the urgent removal of the puncture needle 140 is generated while the patient is punctured with the puncture needle 140.

The puncture needle 140 is a biopsy needle used to puncture a subject under X-ray fluoroscopy by CT to collect and examine a tissue. The puncture needle 140 includes an inner needle having a hook-shaped leading end and a tubular needle tube in which the inner needle is accommodated. The puncture needle 140 collects the tissue by taking in and out the inner needle from the leading end of the needle tube.

The puncture needle is not limited to that of Embodiment 1, but a puncture needle for other purposes such as a radiofrequency therapy puncture needle may be used as the puncture needle.

The upper arm 151 and the lower arm 152 can also be configured such that a distance between the frame 160 and the puncture needle 140 is lengthened by interposing an extending member in the middle as necessary.

In the puncture robot 1A, a second casing (not illustrated) electrically connected to the first casing 11A of the robot body 10A includes the control device (for example, a Personal Computer (PC)) that controls the puncture robot 1A. Each actuator in the robot body 10A, the rotation shaft driving motor 189 that rotates the advancing and retracting shaft 164 provided in the frame 160 of the puncture unit 30A, and the frame rotating motor 175 that rotates the first frame 161 provided in the base 170 of the puncture unit 30A can be operated by the control device. A worker who performs puncture work issues an operation instruction using an operation tool (controller) electrically connected to the PC, whereby the puncture robot 1A is operated according to the operation instruction. The control device of the puncture robot 1A acquires detection signals of the upper sensor 211 and the lower sensor 212, and can measure puncture force when puncturing the subject with the puncture needle 140. The control device of the puncture robot 1A can instantaneously puncture a puncture region of the patient using the puncture needle 140 by operating the air cylinder 220 according to an operation instruction from an operation tool by the operator. The control device of the puncture robot 1A automatically moves the moving end 20A in the advancing and retracting direction, the vertical direction, and the crosswise direction using the linear motion joint by performing a predetermined operation setting, and the leading end (needle point) of the puncture needle 140 can be prevented from moving from a predetermined three-dimensional position even if the arm 150 is operated. Consequently, the angle of the puncture needle 140 can easily be adjusted without moving the leading end of the puncture needle 140 while the leading end (needle point) of the puncture needle 140 is brought close to the puncture region of the patient.

In the puncture robot 1A having the above configuration, the puncture unit 30A can be moved to a desired position by driving the robot body 10A. Thus, the puncture position of the puncture needle 140 can be adjusted. The puncture unit 30A can rotate with the connecting rod 13A as the rotation shaft by driving the connecting rod actuator of the robot body 10A. Using the frame rotating motor 175 that rotates the first frame 161 provided in the base 170 of the puncture unit 30A, posture changing motion can be performed in the biaxial direction of the puncture needle 140, and a puncture angle of the puncture needle 140 can be adjusted.

Specifically, in the puncture robot 1A, the frame 160 swings about the pivot shaft 194 by driving the frame rotating motor 175, the frame 160 is inclined, the sensor holder 153 rotates by the operations of the upper arm 151 and the lower arm 152, which are linked with each other via the frame 160, the puncture needle 140 integrally connected to the front end side of the sensor holder 153 rotates, and the puncture needle 140 is inclined at the same angle as the angle at which the frame 160 is inclined. Thus, for example, the posture of the puncture needle 140 can be changed in a small space inside the CT gantry, and the operability of the puncture robot 1A is improved.

In the puncture robot 1A of Embodiment 2, the rotation shaft driving motor 189 that advances and retracts the puncture needle 140 and the frame rotating motor 175 that changes the rotation center of the posture of the puncture needle 140 are disposed behind the frame 160. This enables the rotation shaft driving motor 189 and the frame rotating motor 175 to be arranged outside the CT gantry during the puncture work under X-ray fluoroscopy by CT. Thus, these driving motors do not affect the CT image, but operability of the puncture robot 1A is improved.

In the puncture robot 1A of Embodiment 2, the puncture operation of the puncture needle 140 is performed by the rotation shaft driving motor 189, the operation to change the inclination of the puncture needle 140 is performed by the frame rotating motor 175, and these operations can independently be performed.

In the puncture robot 1A of Embodiment 2, the upper sensor 211 and the lower sensor 212, which are each constructed with a six-axis force sensor, are vertically stacked on the leading end sides of the upper arm 151 and the lower arm 152. Consequently, the detection signals of the upper sensor 211 and the lower sensor 212 can be acquired to measure the puncture force when the subject is punctured with the puncture needle 40. The upper sensor 211 and the lower sensor 212, which measure the force during puncture, can be disposed as close to the puncture needle 140 as possible and outside the CT gantry. As a result, it can be applied to design of an interface for monitoring a puncture state and presenting the puncture force to a practitioner to improve remote operability.

In the puncture robot 1A of Embodiment 2, the puncture work can be performed in the vicinity of the gantry of CT irradiating X-rays instead of the practitioner, and X-ray exposure of the practitioner can be prevented.

In the puncture robot 1A of Embodiment 2, by disposing the linear guide in the frame 160, the puncture needle 140 can be moved in the puncture direction as soon as possible while the vibration generated in the puncture needle 140 is prevented. This enables the accuracy to be improved in the puncture operation.

In the puncture robot 1A of Embodiment 2, the puncture needle 140 is attached to the air cylinder 220 with the needle grip 230 and the needle grip arm fixture 240 interposed therebetween, so that the air cylinder 220 can perform an instant advancing operation (an operation to penetrate a patient's skin) of the puncture needle 140 with a short stroke in the puncture direction. Consequently, the instantaneous puncturing operation can be performed at the same level as a manual puncture operation by a doctor.

In the puncture robot 1A of Embodiment 2, the needle grip 230 can easily be attached to the leading end sides (the front side of the air cylinder 220) of the upper arm 151 and the lower arm 152 using the two fixing pins 231, and the attachment and detachment of the puncture needle 140 can easily be performed by fastening and releasing the snap lock 290 and by opening and closing the left needle grip arm 260 and the right needle grip arm 270 to the left and right. Consequently, the practitioner can cleanly perform the attachment and replacement of the puncture needle 140, and the puncture needle 140 and its surroundings can be kept clean. For example, the practitioner simply inserts the sterilized needle grip 230 in the air cylinder fixture 300 and then inserts the fixing pins 231, thereby completing the attachment. Thus, the puncture needle 140 is sandwiched and held from both sides by the left needle grip arm 260 and the right needle grip arm 270. After the puncture needle 140 is sandwiched and held from the left and right by the left needle grip arm 260 and the right needle grip arm 270, and the left needle grip arm 260 and the right needle grip arm 270 are closed and locked by the snap lock 290, and thereby completing the grip of the puncture needle 140. In operating the puncture robot, it is very important to secure a clean area and to easily set up a replacement part such as a puncture needle. According to the puncture robot 1A of Embodiment 2, these can be achieved. Depending on the kind of the puncture needle, the shapes of the left needle grip arm and the right needle grip arm can appropriately be changed.

INDUSTRIAL APPLICABILITY

The puncture robot of the present invention can be used in medical puncture work, and for example, it is useful when the puncture is performed while the position of a tumor and the position of the puncture needle are checked under the X-ray fluoroscopy by CT.

DESCRIPTION OF REFERENCE SIGNS 1, 1A: Puncture robot
30, 30A: Puncture unit
40, 140: Puncture needle
50, 150: Arm
51, 151: Upper arm
52, 152: Lower arm
60, 160: Frame
61, 161: First frame
62, 162: Second frame
63, 163: Connecting rod
64, 164: Advancing and retracting shaft
70, 170: Base
220: Air cylinder (actuator)

The invention claimed is:
1. A puncture robot comprising: a robot body; and a puncture unit attached to a moving end, the moving end being provided to the robot body and movable in any direction, wherein the puncture unit includes:

an arm in which a puncture needle is attached to a leading end of the arm;

a frame to which a base end of the arm is attached; and a base that supports the frame, the frame includes a first frame, a second frame, and a connecting rod, each of the first frame and the second frame having a rectangular frame shape and having an advancing and retracting shaft such that the advancing and retracting shaft of the first frame is provided inside the first frame and the advancing and retracting shaft of the second frame is provided inside the second frame, the connecting rod connecting the first frame and the second frame while the first frame and the second frame are opposite each other, the arm includes an upper arm for supporting a base end side of the puncture needle and a lower arm for supporting a leading end side of the puncture needle with respect to a portion supported by the upper arm, and holds the puncture needle attached in parallel to the advancing and retracting shafts, the puncture needle is advanced and retracted in a puncture direction by advancing and retracting the upper arm and the lower arm along the advancing and retracting shafts, and the advancing and retracting shaft of the first frame and the advancing and retracting shaft of the second frame are respectively rotatable about a longitudinal axis of the advancing and retracting shaft of the first frame and a longitudinal axis of the advancing and retracting shaft of the second frame.

2. The puncture robot according to claim 1, wherein a first sensor constructed with a six-axis force sensor is provided in a middle portion of the upper arm, and a second sensor constructed with a six-axis force sensor is provided in a middle portion of the lower arm.

3. The puncture robot according to claim 2, wherein the upper arm and the lower arm are bent in a crank shape to offset the puncture needle in the puncture direction.

4. The puncture robot according to claim 3, wherein in the upper arm and the lower arm, a portion that is closer to the puncture needle than the first sensor and the second sensor is made of a resin material.

5. The puncture robot according to claim 2, wherein in the upper arm and the lower arm, a portion that is closer to the puncture needle than the first sensor and the second sensor is made of a resin material.

* * * * *